(12) United States Patent
Di Martino et al.

(10) Patent No.: US 11,521,741 B2
(45) Date of Patent: Dec. 6, 2022

(54) METHODS, SYSTEMS, AND COMPUTER READABLE MEDIA FOR EVALUATING RISKS ASSOCIATED WITH VASCULAR PATHOLOGIES

(71) Applicants: Elena Di Martino, Calgary (CA); Flavio Bellacosa Marotti, Turi (IT); Giampaolo Martufi, Vasteras (SE)

(72) Inventors: Elena Di Martino, Calgary (CA); Flavio Bellacosa Marotti, Turi (IT); Giampaolo Martufi, Vasteras (SE)

( * ) Notice: Subject to any disclaimer, the term of this patent is extended or adjusted under 35 U.S.C. 154(b) by 895 days.

(21) Appl. No.: 16/341,791

(22) PCT Filed: Oct. 16, 2017

(86) PCT No.: PCT/CA2017/051226
§ 371 (c)(1),
(2) Date: Apr. 12, 2019

(87) PCT Pub. No.: WO2018/068153
PCT Pub. Date: Apr. 19, 2018

(65) Prior Publication Data
US 2021/0343405 A1    Nov. 4, 2021

Related U.S. Application Data

(60) Provisional application No. 62/408,460, filed on Oct. 14, 2016.

(51) Int. Cl.
*G16H 50/20* (2018.01)
*G16H 30/40* (2018.01)
*G06T 7/00* (2017.01)

(52) U.S. Cl.
CPC .......... *G16H 50/20* (2018.01); *G06T 7/0012* (2013.01); *G16H 30/40* (2018.01); *G06T 2207/10081* (2013.01); *G06T 2207/10088* (2013.01)

(58) Field of Classification Search
CPC ........ G16H 50/20; G16H 30/40; G16H 30/20; G16H 50/50; G06T 7/0012;
(Continued)

(56) References Cited

U.S. PATENT DOCUMENTS 9,149,065 B2     10/2015   Kleinstreuer
10,748,289 B2 *   8/2020   Tolkowsky ............ A61B 5/021
(Continued)

FOREIGN PATENT DOCUMENTS

WO     2006062958 A2    6/2006
WO     2010099016 A1    9/2010
WO     2014163334 A1    10/2014

OTHER PUBLICATIONS

Extended European Search Report; European Patent Office; European Patent Application No. 17860408.8; dated Feb. 25, 2020; 8 pages.
(Continued)

*Primary Examiner* — Brandon J Miller
(74) *Attorney, Agent, or Firm* — Taft Stettinius & Hollister LLP

(57) ABSTRACT

Provided are methods for estimating a Reserve Strength Ratio in a segment of a blood vessel or a lymphatic vessel. In some embodiments, the methods include providing a multiphase Digital Imaging and Communications in Medicine (DICOM) stack of computed tomography (CT) or magnetic resonance (MR) images of a blood vessel or a lymphatic vessel to software, wherein the stack of DICOM images is organized by phase; providing the output from the software to a Model Segmentation procedure in which the first phase of the DICOM stack (1st phase) is segmented to create the Geometric Model and finite element mesh of the 1st phase and a map of Local Thickness Measure; uploading
(Continued)

a mesh created for the first phase onto the DICOM image volume; mapping each voxel position of the mesh for the first phase to all the subsequent meshes using an optical flow (OF) algorithm; creating deformed meshes at all phases from the maps of displaced nodes; estimating local curvature at each node location for all the phases using a finite difference method; evaluating the local deformation at each phase from the meshes corresponding to all the phases using an element approach; calculating local thickness at each node for all the phases using the deformation calculation at each phase and the thickness measured at the first phase and using the assumption of incompressibility for the aortic wall; and calculating the local principal stresses for each element from an extension of Laplace's equation applied to the local principal directions of curvatures, whereby the Reserve Strength Ratio in a segment of a blood vessel or a lymphatic vessel is estimated. Also provided are methods for predicting an increased risk of rupture of a blood vessel or a lymphatic vessel, methods for identifying subjects as being at risk for rupture of a blood vessel or a lymphatic vessel, and computer program products with computer executable instructions embodied in computer readable medium for performing the methods disclosed herein.

9 Claims, 4 Drawing Sheets

(58) Field of Classification Search
CPC . G06T 2207/10081; G06T 2207/10088; G06T 2207/30104; G06T 7/64; G06T 17/20; G01R 33/20
See application file for complete search history.

(56) References Cited

U.S. PATENT DOCUMENTS

| | | | |
|---|---|---|---|
| 2006/0069318 A1* | 3/2006 | Keaveny | G06T 7/97 703/11 |
| 2007/0232883 A1* | 10/2007 | Ilegbusi | A61B 8/4416 600/407 |
| 2008/0137929 A1 | 6/2008 | Chen et al. | |
| 2015/0262388 A1 | 9/2015 | Toshiba et al. | |
| 2016/0027340 A1 | 1/2016 | Chiribiri et al. | |

OTHER PUBLICATIONS

A. Delfino et al.; Residual Strain Effects on the Stress Field In a Thick Wall Finite Element Model of the Human Carotid Bifurcation; J. Biomechanics; 1997; 10 pages; vol. 30, No. 8.
Thomas C. Gasser et al.; A Three-Dimensional Finite Element Model for Arterial Clamping; Journal of Biomechanical Engineering; Aug. 2002; 10 pages; vol. 124.
International Search Report; Canadian Intellectual Property Office; International Application No. PCT/CA2017/051226; dated Jan. 23, 2018; 3 pages.
Written Opinion of the International Searching Authority; Canadian Intellectual Property Office; International Application No. PCT/CA2017/051226; dated Jan. 23, 2018; 4 pages.

* cited by examiner

METHODS, SYSTEMS, AND COMPUTER READABLE MEDIA FOR EVALUATING RISKS ASSOCIATED WITH VASCULAR PATHOLOGIES

CROSS REFERENCE TO RELATED APPLICATION

This application is a U.S. National Phase of International PCT Application No. PCT/CA2017/0051226 filed Oct. 16, 2017, which claims the benefit of U.S. Provisional Patent Application Ser. No. 62/408,460 filed Oct. 14, 2016, the contents of each application are incorporated herein by reference in their entirety.

TECHNICAL FIELD

The presently disclosed subject matter relates generally to methods, systems, and computer readable media for evaluating risks associated with vascular pathologies. In particular, the presently disclosed subject matter relates to employing a measure referred to as Reserve Strength Ratio for evaluating such risks.

BACKGROUND

Aortic aneurysms (abdominal and thoracic) are generally asymptomatic and indolent. If left untreated, an aneurysm will gradually expand until rupture; an event that carries a mortality rate of 90%. The commonly used maximum diameter criterion is based on a statistically-derived cut-off value and when used alone to provide indication for surgery is prone to false positives and false negatives. Surgery treatments, both open and minimally invasive endovascular approaches, present immediate as well as long term risks to the patient and should be reserved to the cases where the risk of complications outweighs surgical risks. Thus, methods to improve risk assessment for life-threatening events such as aortic rupture and dissection would be desirable, particularly where a treatment itself can have its own complications and is reserved for those aneurysms at highest risk of rupture.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides methods for estimating a Reserve Strength Ratio (RSR) and a Maximum Pressure Strength (MPS) in a segment of a blood vessel or a lymphatic vessel. In some embodiments, the methods comprise providing a multiphase Digital Imaging and Communications in Medicine (DICOM) stack of computed tomography (CT) or magnetic resonance (MR) images of a blood vessel or a lymphatic vessel to software, wherein the stack of DICOM images is organized by phase; providing the output from the software to a Model Segmentation procedure in which the first phase of the DICOM stack (1st phase) is segmented to create the Geometric Model and finite element mesh of the 1st phase and a map of Local Thickness Measure; uploading a mesh created for the first phase onto the DICOM image volume, mapping each voxel position of the mesh for the first phase to all the subsequent meshes using an optical flow (OF) algorithm; creating deformed meshes at all phases from the maps of displaced nodes; estimating local curvature at each node location for all the phases using a finite difference method; evaluating the local deformation at each phase from the meshes corresponding to all the phases using an element approach; calculating the maximum principal strain at each nodal location; calculating local thickness at each node for all the phases using the deformation calculation at each phase and the thickness measured at the first phase and using the assumption of incompressibility for the aortic wall; and calculating the local principal stresses for each element from an extension of Laplace's equation applied to the local principal directions of curvatures, wherein the Reserve Strength Ratio in a segment of a blood vessel or a lymphatic vessel is calculated. In some embodiments, the local strength estimated is used to calculate the Maximum Pressure Strength by calculating the pressure equivalent that would raise the stress in each segment of the vessel above the estimated strength. In some embodiments, the stack of DICOM images is organized by phase with the number of phases being based at least in part on whether the images are CT images or MR images. In some embodiments, the segmentation from the first phase of the DICOM phase also provides a measure for the thickness of the wall at each of the nodes of the mesh.

The presently disclosed subject matter also provides in some embodiments methods for predicting an increased risk of rupture of a blood vessel or a lymphatic vessel. In some embodiments, the methods comprise calculating a Reserve Strength Ratio in a blood vessel or a lymphatic vessel in a subject; and identifying at least one region of the blood vessel or the lymphatic vessel for which the Reserve Strength Ratio is less than a pre-selected percentage, whereby an increased risk of rupture of the blood vessel or the lymphatic vessel is predicted. In some embodiments, the pre-selected percentage is selected from the group consisting of 30%, 35%, 40%, 45%, 50%, 55%, 60%, 70%, 75%, 80%, 85%, 90%, 95%, and 100%. In some embodiments, the methods comprise calculating a Maximum Pressure Strength in a blood vessel or a lymphatic vessel in a subject; and identifying at least one region of the blood vessel or the lymphatic vessel for which the Maximum Pressure Strength is less than a pre-selected value chosen by the user based on the vessel of interest. In some embodiments, the pre-selected value is selected from the group consisting of 130 mm Hg, 120 mm Hg, 110 mm Hg, 100 mm Hg, 90 mm Hg, 80 mm Hg, 70 mm Hg. 60 mm Hg, and 50 mm Hg. In some embodiments, the vessel is the abdominal aorta and the pre-selected value is 100 mm Hg.

The presently disclosed subject matter also provides in some embodiments methods for identifying subjects as being at risk for rupture of a blood vessel or a lymphatic vessel. In some embodiments, the methods comprise calculating a Reserve Strength Ratio in a blood vessel or a lymphatic vessel in a subject, wherein presence of at least one region of the blood vessel or the lymphatic vessel for which the Reserve Strength Ratio is less than a pre-selected percentage identifies the subject as being at risk for rupture of the blood vessel or the lymphatic vessel. In some embodiments, the pre-selected percentage is selected from the group consisting of 15%, 20%, 25%, 30%, 35%, 40%, 45%, 50%, 55%, 60%, 70%, 75%, 80%, 85%, 90%, 95%, and 100%.

The presently disclosed subject matter also provides in some embodiments methods for identifying subjects as being at risk for rupture of a blood vessel or a lymphatic vessel. In some embodiments, the methods comprise calculating a Reserve Strength Ratio (RSR), a Maximum Pressure Strength (MPS), or both in a blood vessel or a lymphatic vessel in a subject, wherein presence of at least one region of the blood vessel or the lymphatic vessel for which the RSR and/or the MPS is less than a pre-selected value identifies the subject as being at risk for rupture of the blood vessel or the lymphatic vessel. In some embodiments, the pre-selected value for RSR is selected from the group consisting of 15%, 20%, 25%, 30%, 35%, 40%, 45%, 50%, 55%, 60%, 70%, 75%, 0%, 85%, 90%, 95%, and 100%, and/or the pre-selected value for MPS is selected from the group consisting of 130 mm Hg, 120 mm Hg, 110 mm Hg, 100 mm Hg, 9 mm Hg, 80 mm Hg, 70 mm Hg, 60 mm Hg, and 50 mm Hg.

The presently disclosed subject matter also provides in some embodiments computer program products comprising computer executable instructions embodied in computer readable medium. In some embodiments, the computer program products perform steps comprising accepting data related to a multiphase Digital Imaging and Communications in Medicine (DICOM) stack of computed tomography (CT) or to magnetic resonance (MR) images of a blood vessel or a lymphatic vessel to software, wherein the stack of DICOM images is organized by phase and further wherein the first phase of the DICOM stack (1st phase) is segmented to create the Geometric Model and finite element mesh of the 1st phase and a map of Local Thickness Measure; mapping each voxel position of the mesh for the first phase to all the subsequent meshes using an optical flow (OF) algorithm; creating deformed meshes at all phases from the maps of displaced nodes, estimating local curvature at each node location for all the phases using a finite difference method; evaluating the local deformation at each phase from the meshes corresponding to all the phases using an element approach; calculating local thickness at each node for all the phases using the deformation calculation at each phase and the thickness measured at the first phase and using the assumption of incompressibility for the aortic wall; and calculating the local principal stresses for each element from an extension of Laplace's equation applied to the local principal directions of curvatures.

It is thus an object of the presently disclosed subject matter to provide methods, systems, and computer readable media for evaluating risks associated with vascular pathologies.

An object of the presently disclosed subject matter having been stated hereinabove, and which is achieved in whole or in part by the presently disclosed subject matter, other objects will become evident as the description proceeds when taken in connection with the accompanying Figures and non-limiting examples as best described herein below.

BRIEF DESCRIPTION OF THE FIGURES

Exemplary embodiments of the subject matter described herein will now be explained with reference to the accompanying Figures, wherein like numerals represent like parts, of which.

DETAILED DESCRIPTION

I. Definitions

Figure 1:
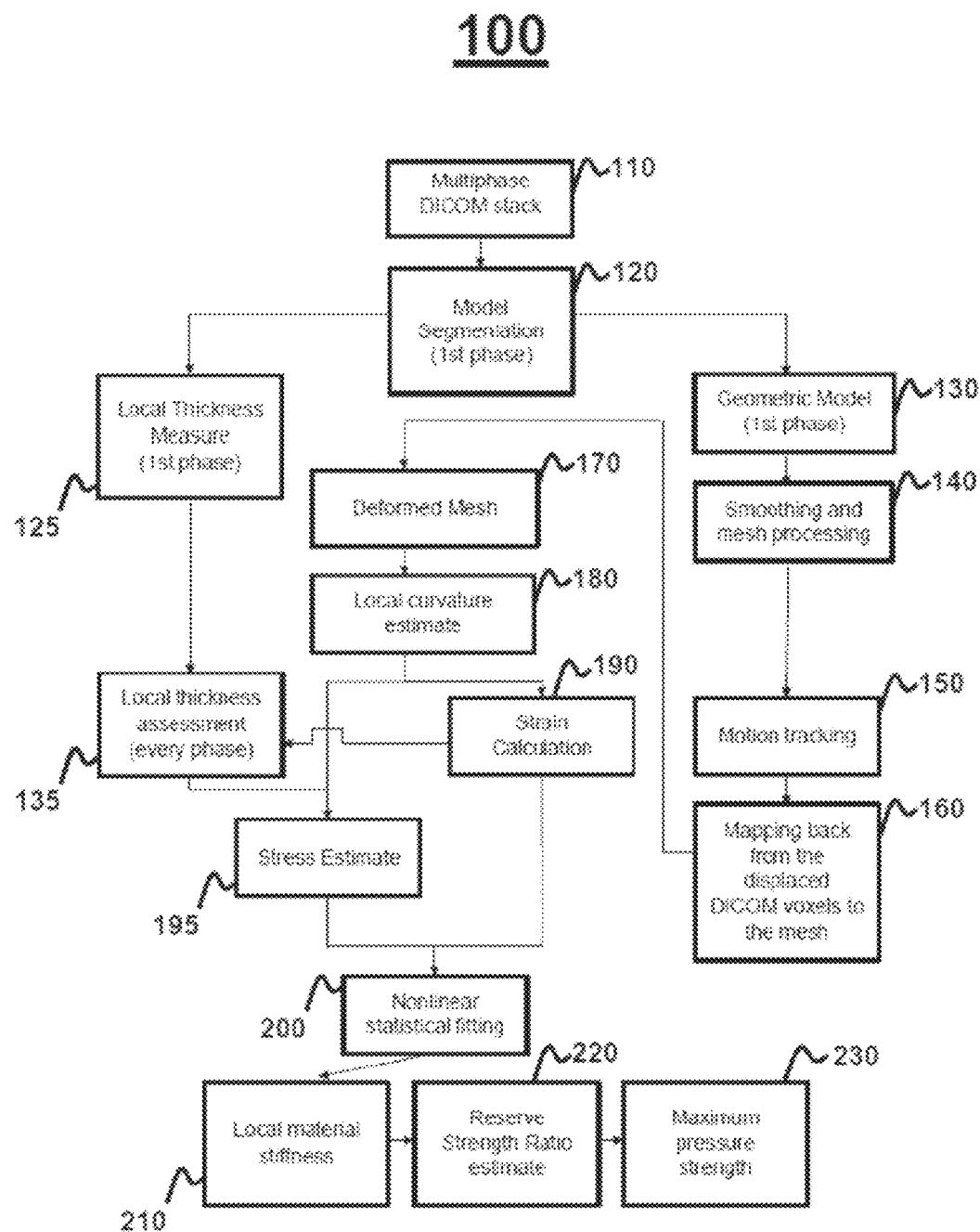
FIG. 1 shows a flow chart of an exemplary embodiment of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood to one of ordinary skill in the art, the following definitions are set forth to facilitate explanation of the presently disclosed subject matter.

All references listed herein, including but not limited to patents, patent application publications, journal articles, and database entries (e.g., GENBANK-4 database entries, including all annotations and references cited therein) are incorporated herein by reference to the extent that they supplement, explain, provide a background for, or teach methodology, techniques, and/or compositions employed herein.

Following long-standing patent law convention, the terms "a", "an", and "the" mean "one or more" when used in this application, including the claims. Thus, the phrase "a flow channel" refers to one or more flow channels, unless the context clearly indicates otherwise.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including", "containing", and "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, and/or ingredient not specifically recited. For example, when the phrase "consists of" appears in a clause of the body of a claim, rather than immediately following the preamble, it limits only the element set forth in that clause, other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising", "consisting essentially of", and "consisting of", where one of these three terms is used herein, the presently disclosed and claimed subject matter can include the use of either of the other two terms.

The term "about", as used herein when referring to a measurable value such as an amount of weight, time, dimension, etc., is meant to encompass variations of in some embodiments 20%, in some embodiments ±10%, in some embodiments ±5%, in some embodiments ±1%, and in some embodiments ±0.1% from the specified amount, as such variations are appropriate to perform the disclosed methods and/or to employ the presently disclosed flow chambers.

II. Method to Determine Structural Strengths of Vessels

The presently disclosed subject matter relates in some embodiments to approaches, including algorithm-based approaches, for determining the actual structural strength of a vessel (e.g., an aorta) in vivo and expresses the same using measures referred to herein as "Reserve Strength Ratio" and "Maximum Pressure Strength" for an individual patient so that clinical decisions can be made with respect to the and on a patient-by-patient basis while taking into account the local heterogeneity of the vessel. In some embodiments, the input comprises a series of dynamic CT scans and/or dynamic MRI images gated over the cardiac cycle. From these inputs, the presently disclosed subject matter is characterized by an output that comprises a complete time-varying strain field in the vessel (e.g., the aorta) in vivo directly from clinical images, without recurring to simulations techniques that have several limiting assumptions No Finite Element Methods techniques were used for these calculations. The presently disclosed approaches thus allows for the computation of local wall strains in a completely non-invasive manner starting from routine CT or MR scans and implicitly includes the combined effect of the pulsatile blood pressure, of the local material properties, and of the surrounding structures. In other words, in some embodiments a fully patient-specific analysis is provided by the presently disclosed subject matter to enable a highly individualized diagnosis (i.e., inter-patient variability) while at the same time taking into account the regional heterogeneity within the aneurysm (i.e. intra-patient variability).

In some embodiments, the presently disclosed subject natter also provides an estimate of the time varying stress acting on the vessel wall, based on curvature changes and intra-luminal pressure.

Figure 4:
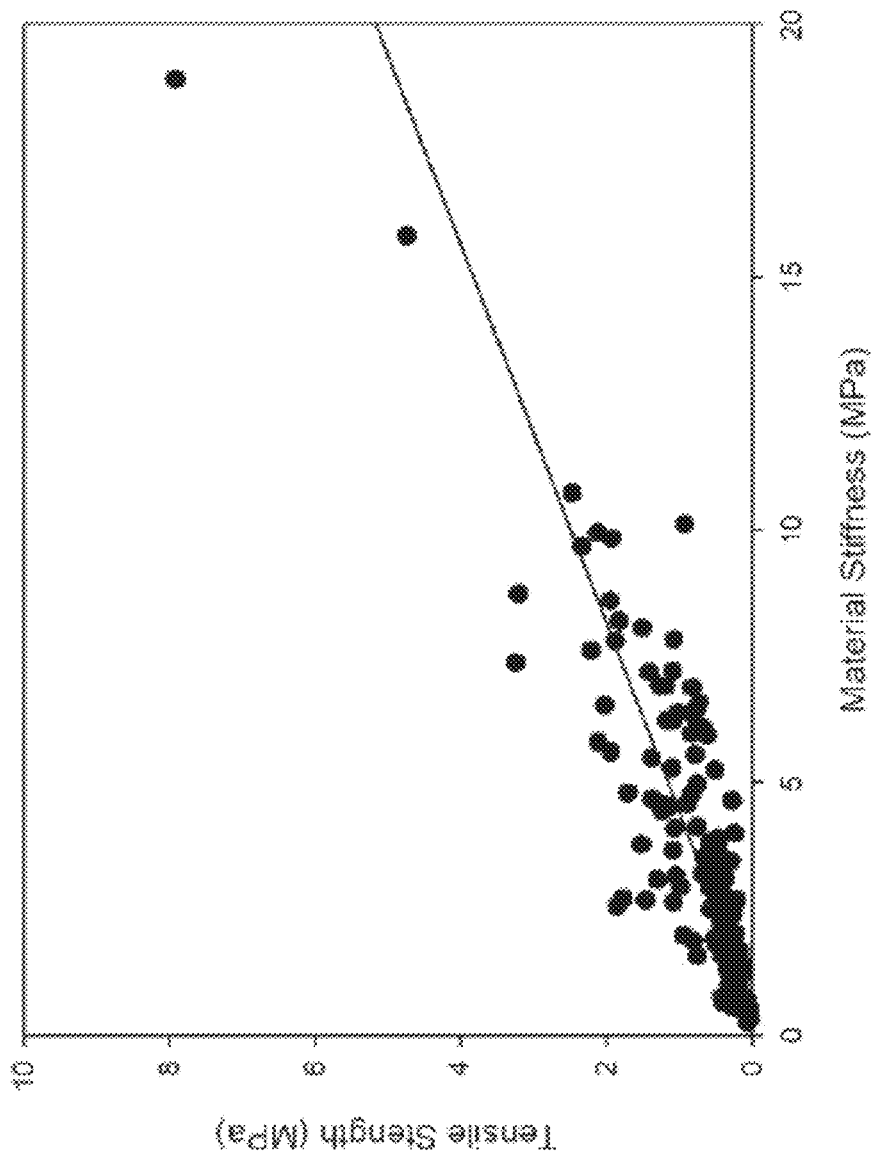
FIG. 4 is a plot of ultimate tensile strength (UTS-MPa) versus material stiffness (MPa) obtained from mechanical tests on specimens obtained from surgery.

In some embodiments, the presently disclosed subject matter also provides an estimate of the strength of the vessel locally. The estimate is based on the observation that strength is directly correlated with the material stiffness of the tissue and inversely correlated with the tissue thickness (FIG. 4) due to inflammation in the tissue that reduces stiffness and increases thickness.

In some embodiments the presently disclosed subject matter also provides a calculation referred to herein as the Reserve Strength Ratio. At each point on the vessel wall, the presently disclosed subject matter allows for a calculation of a % index of strength that indicates how vulnerable to rupture and/or dissection the vessel wall is in real time.

In some embodiments the presently disclosed subject matter also provides a calculation referred to herein as the Maximum Pressure Strength. At each point on the vessel wall, the presently disclosed subject matter allows for a calculation of an equivalent blood pressure value that identifies a low-limit blood pressure value that could rupture the vessel at any given location given the calculated strength and the local diameter of the vessel.

By way of example and not limitation, a normal aorta in a healthy subject has a Reserve Strength Ratio of more than 100%. It has been determined that in an aneurysm, values of Reserve Strength Ratio as low as 25-30% can be observed. What this translates to is that for a normal aorta, a pressure of more than 800 mmHg would be required for the aorta to rupture and/or dissect (which in practical terms is impossible), while at 25-30% Reserve Strength Ratio a small increase in pressure or further decrease in mechanical properties would be enough to rupture and/or dissect the aorta. The Maximum Pressure Strength is intended as a demonstrative index to help relate the Reserve Strength Ratio in terms of low-limit pressure equivalent that can cause vessel failure for a specific Reserve Strength Ratio at a specific point.

Localized non-invasive material stiffness estimations could benefit decision making for other pathologies as well. For example, the presently disclosed subject matter could be used to identify fibrotic areas to better target atrial fibrillation. It could also be used for the evaluation of annulus integrity for the selection of candidate patients for catheter-based aortic valve replacement. Finally, it could be used (coupled with force-plate and fluoroscope measurements) to identify local material properties changes in cartilage that precede symptomatic arthritis.

FIG. 1 shows a flow chart of an exemplary embodiment of the presently disclosed subject matter, particularly with respect to exemplary method for calculating Reserve Strength Ratio 100. With respect to dynamic imaging scans acquisition. CT or MR can be used. In some embodiments, a CT protocol can comprise pre-operative retrospectively gated MDCT (64-row multi-slice CT scanner) with variable dose radiation to capture the R-R interval. In some embodiments, an MR protocol can comprise steady slate T2 weighted fast field echo (TE=2.6 ms, TR=5.2 ms, flip angle 110 degree, fat suppression (SPIR), echo time 50 ms, maximum heart phases 2, matrix 256×256, acquisition voxel MPS 1.56/1.56/3.0) mm and reconstruction voxel MPS 0.78/0.78/1.5), or similar cine acquisition of the portion of aorta under study, axial slices.

With particular reference to FIG. 1, the first step of the algorithm relates to multiphase Digital Imaging and Communications in Medicine (DICOM) stack 110. Stack of DICOM images 110 (organized by phase—10 for CT and 30 for MR) is loaded into Matlab software (The MathWorks, Inc., Natick, Mass., United States of America). The output from the Matlab software is then provided to Model Segmentation procedure 120 in which the first phase of DICOM stack 110 (corresponding to the time in the cardiac cycle chosen as phase 0) is segmented to create Geometric Model 130 of phase 0 and map of Local Thickness Measure 125. Geometric Model 130 created is smoothed and a mesh (in some embodiments, discretized geometry in small triangular elements) is created with a resolution at least as big as the pixel size (Smoothing and mesh processing step 140). The mesh created for the first phase is uploaded onto the DICOM image volume (Mesh mapping to the DICOM volume). Each voxel position of the mesh for the first phase is mapped to all the subsequent meshes using an optical flow (OF) algorithm (Motion tracking 150 of the DICOM voxels with OF (every phase)).

The position of all the voxel at the different phases is mapped back to the mesh for the 1st phase (Mapping back from the displaced DICOM voxels to the mesh 160) In essence, each node position of the geometry at the first phase is associated with node positions corresponding to all the subsequent phases. For example, for CT images, the nodes corresponding to the first phase will have corresponding node positions for all the subsequent nine (9) phases. (see Satriano et al. (2015) In vivo strain assessment of the abdominal aortic aneurysm. *J Biomech* 48(2):354-360).

Geometric Model 130 obtained from the segmentation from the first phase of the DICOM phase also provides a measure for the thickness of the wall at each of the nodes of the mesh, (Local Thickness Measure (1st phase) 125; see Shum et al. (2010) Semi-automatic vessel wall detection and quantification of wall thickness in computed tomography images of human abdominal aortic aneurysms. *Medical Physics* 37(2):638-648).

From the maps of displaced nodes, deformed meshes at all phases are created (Deformed Geometric Model Mesh (all phases) 170).

Local curvature is estimated at each node location for all the phases using a finite difference method (Local curvature estimate (each phase) 180; see Rusinkiewicz (2004) Estimating curvatures and their derivatives on triangle meshes. In Proceedings, 2nd International Symposium on 3D Data Processing, Visualization and Transmission, 2004. 3DPVT 2004. Institute of Electrical & Electronics Engineers (IEEE).

From the meshes corresponding to all the phases, the local deformation at each phase is evaluated by means of an element approach (Deformation Calculation; see Satriano et al. (2015) In vivo strain assessment of the abdominal aortic aneurysm *J Biomech* 48(2):354-360).

Using the deformation calculation at each phase, the thickness measured at the first phase and using the assumption of incompressibility for the aortic wall (as is widely accepted), local thickness is calculated at each node for all the phases (Local thickness assessment 135 (every phase)).

Thanks to the tubular symmetry of the TAA structure, the local principal stresses are calculated for each element from an extension of Laplace's equation applied to the local principal directions of curvatures (Stress Estimate 195). This algorithm uses the local deformation, the local principal curvatures, the pressure measured from the patient, and the local thickness (as computed above).

In some embodiments, the outputs of the complete algorithm are:
Local Stress along the principal directions of curvature (at every phase);
Local Strain along the principal directions of curvature (at every phase); and
Local Maximum Principal Strain along the principal strain direction (at every phase)

Nonlinear statistical fitting procedure 200 provides local Material Stiffness estimate 210, Reserve Strength Ratio estimate 220 and Maximum Pressure Strength estimate 230. In some embodiments, the local mechanical properties of the aorta are estimated through non-linear statistical fitting (equivalent stiffness, neo-Hookean material parameter, non-linear anisotropic constitutive model material parameters) and the Reserve Strength Ratio is estimated from the local material properties using the statistical fitting procedure. Local strain calculation 190 comes directly from deformed mesh 170. Continuum mechanics methods are employed to obtain a deformation gradient tensor at each phase from deformed mesh 170 and then from the deformation gradient tensor the different strain measures are computed: maximum principal strain and strain projected along circumferential and axial directions.

III. Methods for Computing a Reserve Strength Ratio (RSR) of a Vessel

In some embodiments, the presently disclosed subject matter relates to methods for computing a Reserve Strength Ratio (RSR) of a vessel. As used herein, the phrase "Reserve Strength Ratio" refers to a local measure that computes a propensity for rupture of a vessel wall tissue including, but not limited to an aortic wall tissue. In some embodiments, RSR can be used as an added diagnostic measure (i.e., in addition to standard diagnostic measures currently employed including, but not limited to diameter, growth rate, subject age, and subject gender) to personalize an evaluation of risk of rupture of aortic aneurysms).

By way of example and not limitation, an exemplary clinical workflow that can be employed with the methods of the presently disclosed subject matter is as follows. Once an aneurysm has been diagnosed (e.g., obtained with an ultrasound scan), a subject undergoes either a) multi-detector CT scan imaging; or b) cine MR imaging. Pressure data are also collected at the time of imaging. The DICOM images and the pressure information are fed to a semi-automated software that computes the local strain and local stress on the individual aortic aneurysm. These local strain and stress measures are in some embodiments outputted as color-coded maps to visualize and identify areas of a vessel wall that are at higher strain (e.g., where the aneurysm Jr wall could be weaker) and areas at elevated stress. Based on the local deformation and local thickness measures, an algorithm of the presently disclosed subject matter computes a local maximum principal strain measure, an anisotropy measure and a thickness measure that are fed into a non-linear regression algorithm that provides a value for the tissue strength at each local point along the aneurysm. The experimental local strength measure (measured from uniaxial tensile tests to failure) was predicted for 44 specimens obtained from surgical resection of aortic aneurysm specimens from five (5) patients using an algorithm of the presently disclosed subject manner with a power>0.8 and p-value<0.05.

The local strength measure is thereafter used along with the local stress measure to compute a Reserve Strength Ratio (RSR) at each point of the aneurysm. The RSR represents a ratio between the applied stress to the aneurysm locally and the actual local strength of the tissue at that location. As a reference, a normal aorta has a Reserve Strength Ratio of >100%. In some embodiments, any areas with a Reserve Strength Ratio of less than 50% are considered weak spots and can be considered by a surgeon and/or a radiologist as possible at risk sites.

Figure 2:
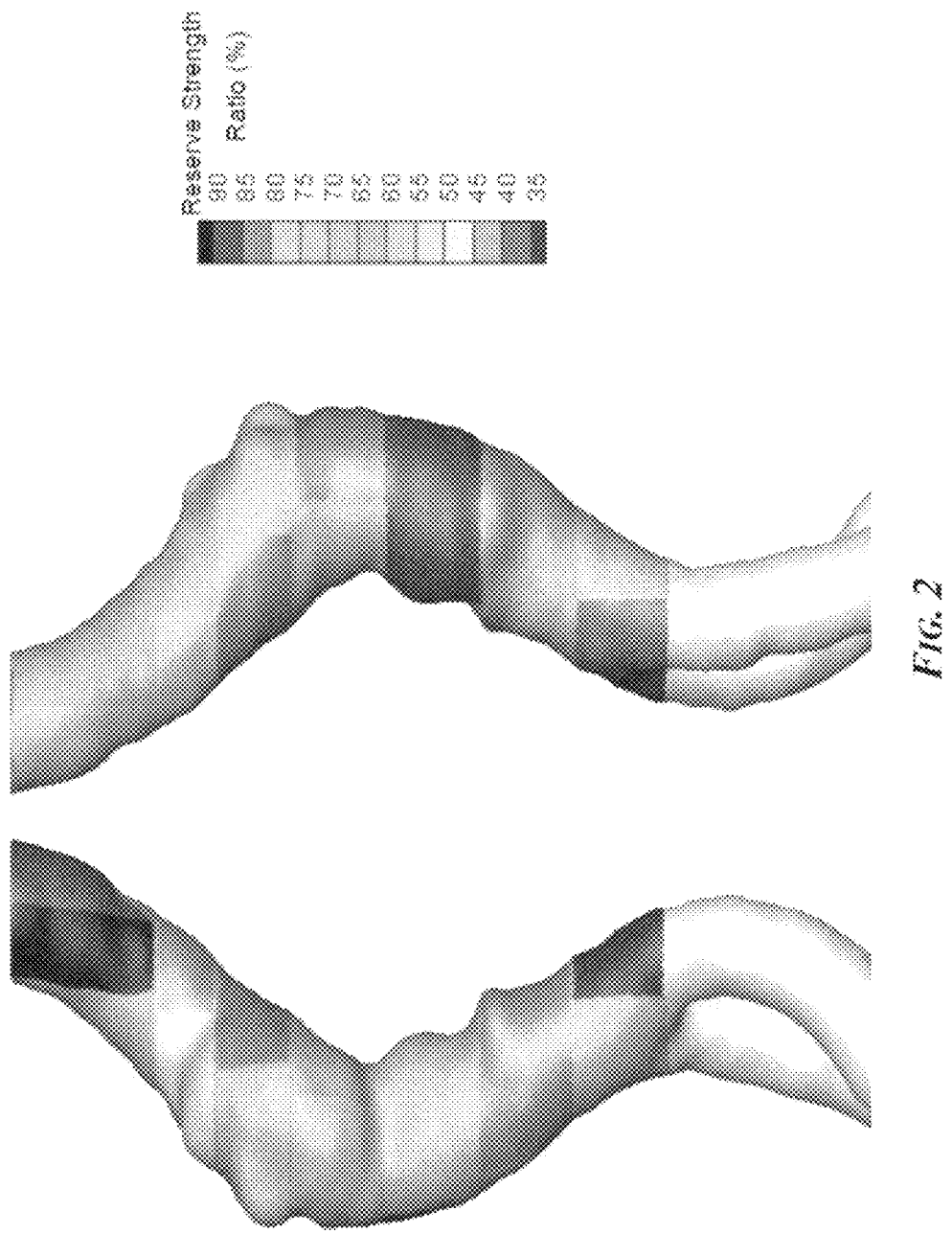
FIG. 2 is a depiction of Reserve Strength Ratios and how they can differ along a segment of an exemplary abdominal aortic aneurysm (AAA) case.
Figure 3:
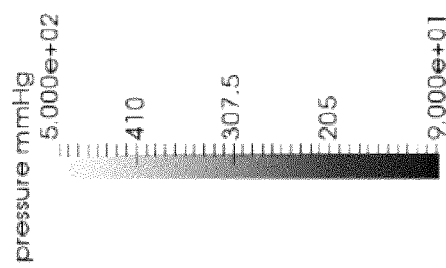
FIG. 3 is a depiction of Maximum Pressure Strength and how it can differ along a segment of an exemplary abdominal aortic aneurysm (AAA) case. Black/Dark grey represents segments at elevated risk of rupture (Maximum Pressure Strength<100 mmHg).
Figure 3:
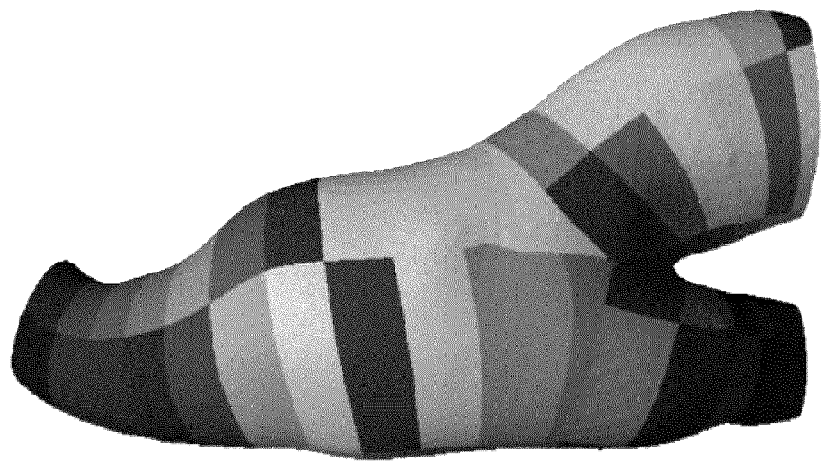

In some embodiments, the Reserve Strength Ratio can be visualized as a color-coded map with different colors indicating weaker areas (see e.g. FIG. 2 for a black and white depiction of an example of a color-coded RSR map).

IV. Methods for Computing a Maximum Pressure Strength from the Strength Estimate Additionally, in some embodiments the presently disclosed subject matter relates to visualization of local wall vulnerability of a vessel as a "Maximum Pressure Strength" measure. Thus, in some embodiments the local strength can be used locally to compute the blood pressure (in mm Ig) that would disrupt the tissue at that location, referred to herein as a "Maximum Pressure Strength".

In some embodiments, the "normal" pressure in a blood vessel or lymphatic vessel is 80-120 mm Hg. Thus, and by way of example and not limitation, the pre-selected value for Maximum Pressure Strength is in some embodiments 130 mm Hg, in some embodiments 120 mm Hg, in some embodiments 110 mm Hg, in some embodiments 100 mm Hg, in some embodiments 9) mm Hg, in some embodiments 80 mm Hg, in some embodiments 70 mm Hg, in some embodiments 60 mm Hg, and in some embodiments 50 mm Hg. In some embodiments, the vessel is the abdominal 1r aorta and the pre-selected value for Maximum Pressure Strength is 100 mm.

In some embodiments, a pressure equivalent measure can provide surgeons, radiologists, and other medical professionals with an immediate readout of the risk of rupture of a particular segment of a vessel including, but not limited to the aorta.

EXAMPLES

The following EXAMPLES provide illustrative embodiments of the presently disclosed subject matter. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Example 1

Analysis of a Representative Abdominal Aortic Aneurysm (AAA)

An analysis of a patient undergoing surgery for an abdominal aortic aneurysm (AAA) was performed with respect to the presently disclosed subject matter. The results are provided in FIG. 2. As shown in FIG. 2, the aorta presented with areas where the Reserve Strength Ratio was 30% (red areas—dark grey in the b/w figure) and areas where the Reserve Strength Ratio was in excess of 80% (blue areas—black in the b/w figure). For comparison, a normal aorta typically has a Reserve Strength Ratio of more than 100%. In the instant case, the patient had a relatively small aorta (4.5 cm maximum diameter) that was below the guidelines for surgery for an abdominal aortic aneurysm. However, the presently disclosed subject matter (confirmed by subsequent material testing) identified some areas of weak aorta that was at risk for rupture.

Example 2

Calculation of RSR

Dynamic diagnostic images are obtained of an entire aneurysm, with sagittal slices of at least 1.5 mm diameter for CT and/or 6 mm for MR. Spatial resolution is at least 1.4 mm in plane for MR and 0.5 mm in plane for CT. Temporal resolution is 10 phases/cardiac cycle for CT images and 30 phases/cardiac cycle for MR, which have been validated in porcine and human cases. Pressure is also measured at the time of the imaging scans. The DICOM images are uploaded into software of the presently disclosed subject matter. The user inputs the subject's pressure and selects the location of the aneurysm and type(s) of images (CT and/or MR).

Thereafter, the user selects the first phase (phase 0) and is prompted to select parameters to build a mesh (including, but not limited to discretization of the 3D geometry in smaller triangular elements). The user also selects parameters for the optical flow algorithm to perform the strain calculation, including number of iteration=5, and spatial coherence=200. The software then computes a strain map and a stress map.

The user thereafter selects desired visualization options for the strain and stress maps as well as other options to calculate the maximum/minimum strain/stress 2Q values and visualize the relative locations. The RSR calculation can then be initiated, with the user selecting options to visualize RSR as a map and/or to visualize the location of the lower RSR value or a map of areas within a user-selected limit. If desired, the user can also select a "equivalent-diameter" calculation to visualize the location and value of the maximum "equivalent-diameter.

Example 3

Validation of RSR Calculation

The principle underlying the RSR calculation was validated on a large sample of intra-operatory specimens (n=116). The results are presented in FIG. 4. Tensile Strength (MPa) and Material Stiffness (MPa) were measured using a uniaxial Tensile testing device (Model 3200; TA Instruments, Eden Prairie, Minn., United States of America) while being continuously wetted with PBS solution. After 10 cycles preconditioning at 10% deformation, the samples were tested to failure while recording the Cauchy Stress and stretch as the deformed length normalized by the original length of each specimen. The material stiffness was calculated as the maximum tangential stiffness of the stress/stretch curve.

The strength of the tissue correlated with the material stiffness (calculated as set forth herein); Pearson's correlation coefficient=0.85. ($p<0.01$). The strength of the tissue also correlated with the thickness of the tissue; Pearson's correlation coefficient=−0.27 ($p<0.01$). The RSR (and maximum pressure strength) calculations were based on an algorithm based on this experimental correlation.

In order to validate the in-vivo estimation of the strength of the tissue, aneurysm aortic patients (n=5) underwent dynamic CT imaging following an approved ethics protocol prior to surgery. During surgery, intra-operatory specimens were collected (n=44) and tensile tests to failure were conducted. Material stiffness was estimated via the maximum principal strain measure (with higher strain meaning lower material stiffness) and wall thickness was categorized as 0 (when thickness<1.9 mm and 1 (when thickness≥1.9 mm). The tensile strength correlated with the local maximum principal strain computed from our algorithm (Pearson's coefficient=−0.5, $p<0.01$). The tensile strength correlated with the Wall thickness (Spearman Rank Order Correlation coefficient=−0.476, $p<0.01$).

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for estimating a Reserve Strength Ratio in a segment of a blood vessel or a lymphatic vessel, the method comprising:
   (a) providing a multiphase Digital Imaging and Communications in Medicine (DICOM) stack of computed tomography (CT) or magnetic resonance (MR) images of a blood vessel or a lymphatic vessel to software, wherein the DICOM stack of images is organized by phase;

(b) providing an output from the software to a Model Segmentation procedure in which a first phase of the DICOM stack ($1^{st}$ phase) is segmented to create a Geometric Model and finite element mesh of the first phase and a map of Local Thickness Measure;

(c) uploading the finite element mesh created for the first phase onto a DICOM image volume;

(d) mapping each voxel position of the finite element mesh for the first phase to all subsequent meshes using an optical flow (OF) algorithm to obtain maps of displaced nodes;

(e) creating deformed meshes at all phases from the maps of displaced nodes;

(f) estimating local curvature at each node location of the deformed meshes for all the phases using a finite difference method;

(g) evaluating local deformation at each phase from the deformed meshes corresponding to all the phases using an element approach;

(h) calculating local thickness at each node for all the phases using the local deformation calculation at each phase and the map of the local thickness measure at the first phase and using an assumption of incompressibility for an aortic wall;

(i) calculating local principal stresses for each element from an extension of Laplace's equation applied to local principal directions of curvatures based on the local deformation, the local curvature, the local thickness and pressure data from a patient; and (j) estimating the Reserve Strength Ratio in the segment of the blood vessel or the lymphatic vessel based on the local principal stresses.

2. The method of claim 1, wherein the DICOM stack of images is organized by phase with the number of phases being based at least in part on whether the DICOM stack of images are CT images or MR images.

3. The method of claim 1, wherein the segmented first phase of the DICOM stack also provides a measure for a thickness of the wall at each of the nodes of the mesh.

4. The method of claim 1, wherein said estimating the Reserve Strength Ratio in the segment of the blood vessel or the lymphatic vessel based on the local principal stresses comprises using a nonlinear statistical fitting procedure.

5. A method for predicting an increased risk of rupture of a blood vessel or a lymphatic vessel, the method being executed by at least one computer processor, the method comprising:

(a) calculating a Reserve Strength Ratio in a blood vessel or a lymphatic vessel in a subject, said calculating the Reserve Strength Ratio comprising:

i. receiving data related to a multiphase Digital Imaging and Communications in Medicine (DICOM) stack of computed tomography (CT) or magnetic resonance (MR) images of a blood vessel or a lymphatic vessel to software, wherein the DICOM stack of images is organized by phase and further wherein a first phase of the DICOM stack (1st phase) is segmented to create a Geometric Model, a finite element mesh of the first phase and a map of Local Thickness Measure;

ii. mapping each voxel position of the finite element mesh for the first phase to all subsequent meshes using an optical flow (OF) algorithm to obtain maps of displaced nodes;

iii. creating deformed meshes at all phases from maps of displaced nodes;

iv. estimating local curvature at each node location for all the phases using a finite difference method;

v. evaluating local deformation at each phase from the deformed meshes corresponding to all the phases using an element approach;

vi. calculating local thickness at each node for all the phases using the local deformation calculation at each phase and the map of local thickness measure at the first phase and using an assumption of incompressibility for an aortic wall;

vii. calculating local principal stresses for each element from an extension of Laplace's equation applied to local principal directions of curvatures based on the local deformation, the local curvature, the local thickness and pressure data from a patient; and viii. estimating the Reserve Strength Ratio in each region of the segment of the blood vessel or the lymphatic vessel based on the local principal stresses;

(b) comparing the Reserve Strength Ratio in each region with a pre-selected percentage to identify at least one region of the blood vessel or the lymphatic vessel for which the Reserve Strength Ratio is less than the pre-selected percentage, wherein the pre-selected percentage is selected from the group consisting of 15%, 20%, 25%, 30%, 35%, 40%, 45%, 50%, 55%, 60%, 70%, 75%, 80%, 85%, 90%, 95%, and 100%; and (c) predicting an increased risk of rupture of the blood vessel or the lymphatic vessel based on the Reserve Strength Ratio being less than the pre-selected percentage.

6. A method for predicting an increased risk of rupture of a blood vessel or a lymphatic vessel, the method being executed by at least one computer processor, the method comprising:

(a) calculating a Maximum Pressure Strength (MPS) in a blood vessel or a lymphatic vessel, said calculating the MPS comprising:

i. receiving data related to a multiphase Digital Imaging and Communications in Medicine (DICOM) stack of computed tomography (CT) or magnetic resonance (MR) images of a blood vessel or a lymphatic vessel to software, wherein the DICOM stack of images is organized by phase and further wherein a first phase of the DICOM stack (1st phase) is segmented to create a Geometric Model, a finite element mesh of the first phase and a map of Local Thickness Measure;

ii. mapping each voxel position of the finite element mesh for the first phase to all subsequent meshes using an optical flow (OF) algorithm to obtain maps of displaced nodes;

iii. creating deformed meshes at all phases from maps of displaced nodes;

iv. estimating local curvature at each node location for all the phases using a finite difference method;

v. evaluating local deformation at each phase from the deformed meshes corresponding to all the phases using an element approach;

vi. calculating local thickness at each node for all the phases using the local deformation calculation at each phase and the map of local thickness measure at the first phase and using an assumption of incompressibility for an aortic wall;

vii. calculating local principal stresses for each element from an extension of Laplace's equation applied to local principal directions of curvatures based on the local deformation, the local curvature, the local thickness and pressure data from a patient; and viii. estimating the Maximum Pressure Strength in each region of the segment of the blood vessel or the lymphatic vessel based on the local principal stresses;

(b) comparing the Maximum Pressure Strength in each region to a pre-selected value to identify at least one region in the blood vessel or lymphatic vessel for which the Maximum Pressure Strength is less than the pre-selected value; and (c) predicting an increased risk of rupture of the blood vessel or the lymphatic vessel based on the Maximum Pressure Strength being less than the pre-selected percentage.

7. The method of claim 6, wherein the pre-selected value is selected from the group consisting of 130 mm Hg, 120 mm Hg, 110 mm Hg, 100 mm Hg, 90 mm Hg, 80 mm Hg, 70 mm Hg, 60 mm Hg, and 50 mm Hg.

8. A non-transitory computer readable medium comprising computer executable instructions executable by at least one processor for performing steps comprising:

(a) accepting data related to a multiphase Digital Imaging and Communications in Medicine (DICOM) stack of computed tomography (CT) or magnetic resonance (MR) images of a blood vessel or a lymphatic vessel to software, wherein the DICOM stack of images is organized by phase and further wherein a first phase of the DICOM stack ($1^{st}$ phase) is segmented to create a Geometric Model and finite element mesh of the first phase and a map of Local Thickness Measure;

(b) mapping each voxel position of the finite element mesh for the first phase to all subsequent meshes using an optical flow (OF) algorithm to obtain maps of displaced nodes;

(c) creating deformed meshes at all phases from maps of displaced nodes;

(d) estimating local curvature at each node location for all the phases using a finite difference method;

(e) evaluating local deformation at each phase from the deformed meshes corresponding to all the phases using an element approach;

(f) calculating local thickness at each node for all the phases using the local deformation calculation at each phase and the map of local thickness measure at the first phase and using an assumption of incompressibility for an aortic wall; and (g) calculating local principal stresses for each element from an extension of Laplace's equation applied to local principal directions of curvatures based on the local deformation, the local curvature, the local thickness and pressure data from a patient.

9. The non-transitory computer readable medium of claim 8, further comprising, prior to said calculating the local principal stresses for each element from the extension of Laplace's equation applied to local principal directions of curvatures based on the local deformation, the local curvature and the local thickness comprises:

calculating, by using continuum mechanics on the deformed mesh at all phases, a deformation gradient tensor at each phase; and calculating local principal strain and maximum principal strain.

* * * * *